US006851807B2

(12) United States Patent
Holdeman

(10) Patent No.: US 6,851,807 B2
(45) Date of Patent: Feb. 8, 2005

(54) VISION THERAPY SYSTEM AND METHOD

(75) Inventor: Kari Holdeman, Santee, CA (US)

(73) Assignee: KD Holdings Group, Inc., Santee, CA (US)

( * ) Notice: Subject to any disclaimer, the term of this patent is extended or adjusted under 35 U.S.C. 154(b) by 316 days.

(21) Appl. No.: 10/255,463

(22) Filed: Sep. 25, 2002

(65) Prior Publication Data

US 2004/0057012 A1 Mar. 25, 2004

(51) Int. Cl.[7] .................................................. A61B 3/00
(52) U.S. Cl. ....................................... 351/203; 351/246
(58) Field of Search ................................ 351/201–203, 351/211, 213–215, 220, 222, 224, 233, 237, 239, 242, 243, 246

(56) References Cited

U.S. PATENT DOCUMENTS 4,907,860 A * 3/1990 Noble ........................ 351/203
5,309,185 A * 5/1994 Harper ....................... 351/202
5,363,154 A * 11/1994 Galanter et al. ............ 351/203
2003/0193646 A1 * 10/2003 Liberman .................. 351/203

OTHER PUBLICATIONS

Simons, K. et al., "Artifacts in fusion and stereopsis testing based on red/green dichopitc image separation", Journal of Pediatric Ophthalmology and Strabismus, Sep.–Oct. 1994, 31 (5), p. 290–297.*
Ludlam, W., "Rehabilitation of traumatic bgrain injury with associated visual dysfunction—A case report", Neurorehabilitation, 1996, V6, N3 (Jun.), p. 183–192.*

* cited by examiner

*Primary Examiner*—Brian L. Casler
*Assistant Examiner*—John R Sanders
(74) *Attorney, Agent, or Firm*—Duckor Spradling Metzger & Wynne; Bernard L. Kleinke

(57) ABSTRACT

According to at least one of the disclosed embodiments of the present invention, there is provided a vision therapy system and method which relates to the viewing of differently colored images through a pair of differently colored lenses for the eyes of the user, where at least one of the colored images has associated therewith a gray image to help conceal from view a selected portion or all of a selected image when viewed through the lenses.

48 Claims, 4 Drawing Sheets

VISION THERAPY SYSTEM AND METHOD

FIELD OF THE INVENTION

The present invention relates in general to a vision therapy system and a method of using it. Embodiments of the present invention relate more particularly to a vision therapy system and method useful as a therapy for a human eye condition known as strabismus, or other such eye maladies.

BACKGROUND ART

Strabismus is a disorder of the muscles of the human eye and may cause the misalignment of the two eyes. This condition may be called "cross eyes" or "wall eyes." A person so afflicted may experience difficulty in focusing both eyes on the same point at the same time. As a result, the brain accommodates by recognizing the images visualized by only one of the two eyes.

Such a malady has been treated by means of surgery to help correct the condition.

There have also been proposed a variety of different therapy techniques for eye maladies. For example, reference may be made to the following U.S. patents, each of which is incorporated herein by reference:

| U.S. PAT. NO. | ISSUE DATE |
|---|---|
| 4,294,522 | Oct. 13, 1981 |
| 4,536,065 | Aug. 20, 1985 |
| 4,756,305 | Jul. 22, 1988 |
| 5,206,671 | Apr. 27, 1993 |
| 5,264,877 | Nov. 23, 1993 |
| 5,360,438 | Nov. 1, 1994 |
| 5,452,026 | Sep. 19, 1995 |
| 5,550,602 | Aug. 27, 1996 |
| 5,877,840 | Mar. 2, 1999 |
| 5,900,921 | May 4, 1999 |

In order to attempt to avoid surgery to correct the disorder of strabismus, a technique has been developed to help a person afflicted with this malady to strengthen his or her eye muscles to help focus the eyes properly. The technique employs the use of images of red and green colored symbols or designs, which are viewed through a pair of eyeglasses having one green lens and one red lens. The person attempts to match the colors of the symbols while wearing the eyeglasses. In so doing, one eye is covered with a green lens, and the other eye is covered with a red lens.

As a result, the person wearing the pair of red and green colored eyeglasses see the red design through the green lens, and the green design through the red lens. In this regard, the red design may not have sufficient contrast using the red lens to be able to allow the person to distinguish the image of the red design. Thus, the red design may not be seen through the same colored red lens. Similarly, the green lens was intended to prevent the green image to be seen through the green lens. This technique tends to cause the person to use and to coordinate the use of both eyes to see the complete image. This exercise then tends to train the muscles of the eyes to focus on an object, and thus the brain tends to take into account the images received by both eyes in a proper manner.

However, unlike the red lens, the green lens may not completely conceal from view the green design for at least some applications. Thus, the person may still be able to see a faint image of the green design through the green lens in certain situations.

As a result, such a technique has not been found to be entirely satisfactory for some applications. For example, when children or certain other people use this technique, the faint green image seen through the green lens at least somewhat defeats the purpose of strengthening the eye muscles by causing the person to use both eyes for focusing. In this regard, the user may still be able to see both the red and green images with the same eye, even though to a limited extent, by using only one lens (the green lens).

DETAILED DESCRIPTION OF CERTAIN EMBODIMENTS OF THE INVENTION

Figure 1:
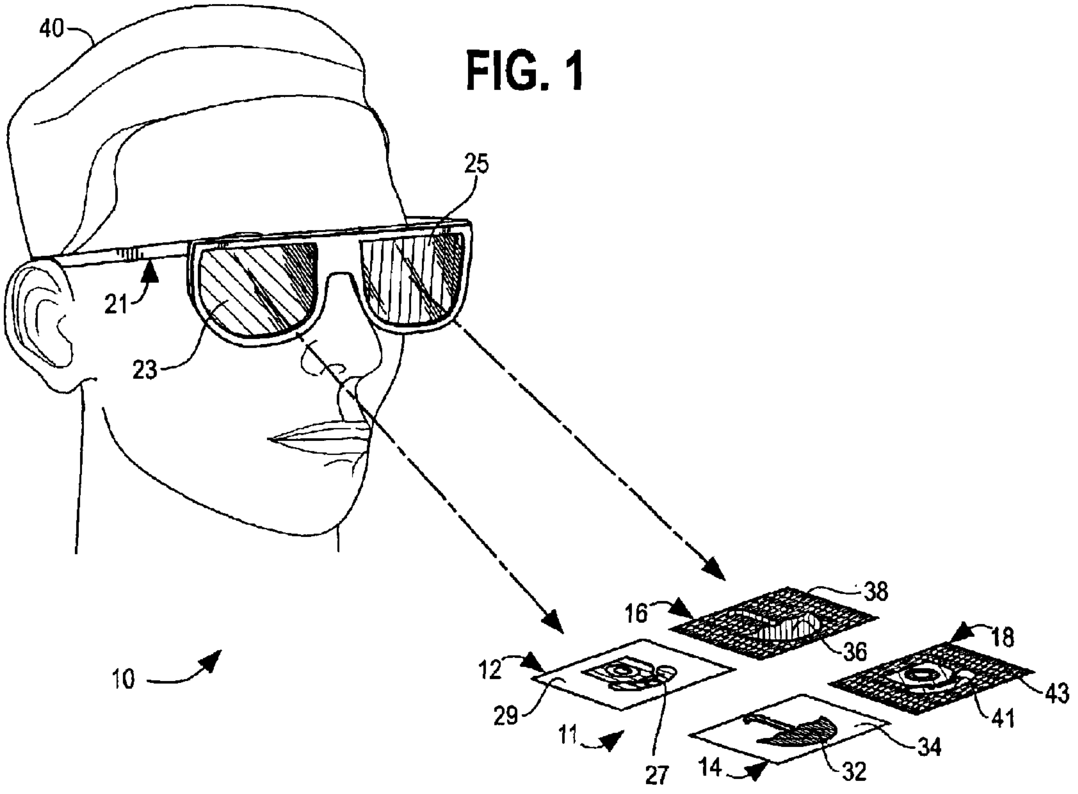
FIG. 1 is a pictorial view of a vision therapy system and method of one example of the present invention.

According to at least one of the disclosed embodiments of the present invention, there is provided a vision therapy system and method which relate to the viewing of differently colored images through a pair of differently colored lenses for the eyes of the user, where at least one of the colored images has associated therewith a gray image to help conceal from view a selected portion or all of a selected image when viewed through the lenses.

According to at least one or more of the embodiments of the present invention, there is provided a vision therapy method and system wherein a first color image is displayed, a second color image is displayed, and a gray image is displayed associated with at least one of the above-mentioned images to conceal selectively from view at least a portion of one of the images when viewed through at least one colored lens.

According to at least another one of the disclosed embodiments of the present invention, a vision therapy method and apparatus includes displaying a red image, displaying a green image, and displaying an image of a gray background for the green image to enable the viewing of the green image through a red lens to add a red component to the green image causing the combined red and green image to appear gray and thus to conceal it from view against the gray background.

Still another vision therapy method and system is disclosed herein in accordance with another embodiment of the present invention includes displaying a grayish-green image, and displaying a gray background image for the grayish-green image to enable the grayish-green image to be viewed through a green lens to add a green component to the gray background and thus to cause the background to conceal the grayish-green image from view.

Referring now to the drawings, and more particularly to FIGS. 1–4 thereof, there is shown a vision therapy system 10, which is constructed in accordance with an embodiment of the present invention. The system 10 includes a group of image bearing cards or sheets generally indicated as 11 including sheets 12, 14, 16 and 18 to provide a matching game, which is entertaining, especially for younger people. A pair of eyeglasses 21 having a pair of differently colored lenses for viewing the image sheets 11, include a green lens 23 and a red lens 25. It should be understood to those skilled in the art that other types and kinds of viewing devices may also be employed. Also, while red and green are the preferred complimentary colors, other colors may also be employed as will become apparent to those skilled in the art.

Figure 2:
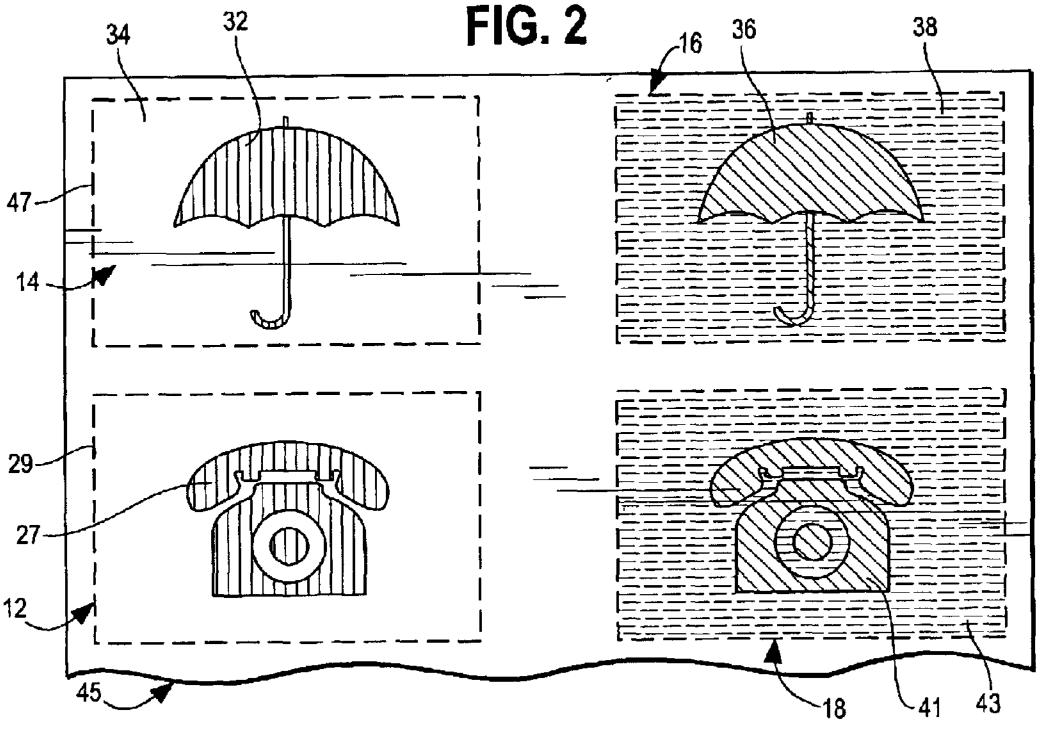
FIG. 2 is an enlarged, fragmentary face view of a portion of a kit forming a part of the system of FIG. 1.

As shown in FIG. 2, there can be several other pairs of red and green colored images (not shown), and can be provided on a page, such as a page 45 which can serve as a kit, or a portion thereof, for the user. The cards or sheets, such as the sheet 14, may be separated from the page 45 along perforations such as perforations 47, or by cutting them out with a scissors (not shown).

The sheet 12 has a red telephone image 27 on the face thereof and is disposed on a white background 29. The sheet 14 has a red umbrella image 32 disposed on a white background 34 on the face thereof. On the sheet 16, there is disposed a grayish-green umbrella image 36 disposed on a gray background 38. The sheet 18 includes on its face a grayish-green telephone image 41 disposed on a gray background 43.

In use, a user 40, as shown in FIG. 1, wears the pair of eyeglasses 21 in a conventional manner, with the green lens 23 covering one eye and the red lens 25 covering the other eye. The user views the individual image sheets and attempts to match similar images thereon. In this case, the user 40 attempts to match the umbrella sheets 14 and 16, and match the telephone image sheets 12 and 18. By utilizing the system 10 of the embodiment of the present invention, the user 40 is compelled to use both eyes to achieve the matching operation. In so utilizing the disclosed embodiment of the invention, the user 40 is assisted in training the brain to rely on the images received by both eyes, rather than only one eye.

Figure 3:
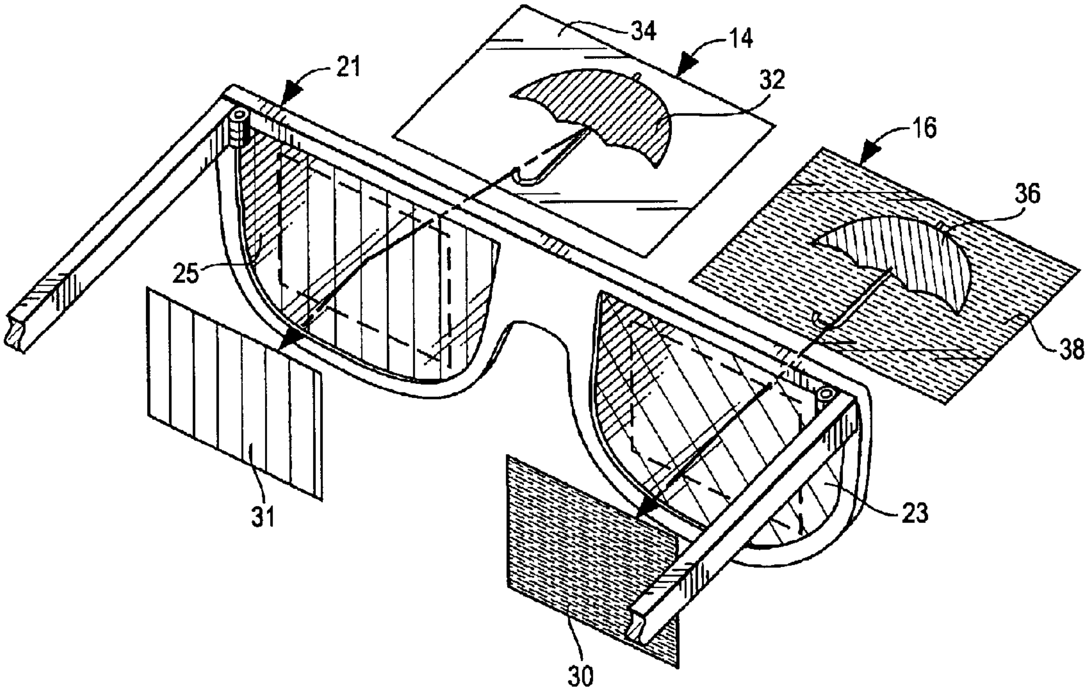
FIGS. 3 and 4 are enlarged pictorial partially diagrammatic views of the system of FIG. 1, illustrating it from the point of view of the user.

When attempting to match two of the image sheets, such as the umbrella image sheets 14 and 16 as indicated in FIG. 3, the green umbrella image 36 is not able to be seen through the green lens 23 as a gray blank image 30 is formed at the eye (in the present example, the right eye). In this regard, the green lens 23 adds a green component to the gray background 38 so that the grayish-green umbrella image 36 is not apparent against the similar grayish-green background as seen through the green lens 23 to form the gray blank image 30 at the right eye of the user.

The red lens 25 provides a red component of color on the white background 34 of the sheet 14, whereby the red umbrella image 32 is not apparent against the reddish background as visualized through the red lens 25 to form a red blank image 31 at the left eye of the user 40. Thus, the green lens 23 blocks from the view of the user 40 the green umbrella image 36, and the red lens 25 blocks from the view of the user 40 the red umbrella image 32.

Figure 4:
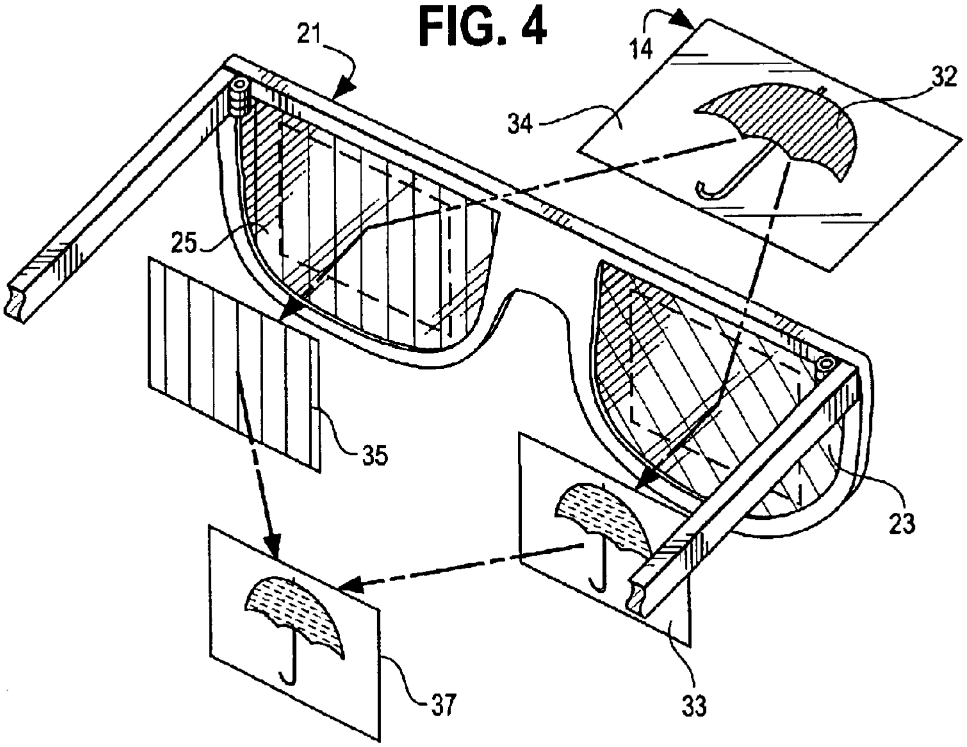

As indicated in FIG. 4, in order for the user 40 to match the images, the user must use both of his or her eyes to visualize the colored images. As indicated in FIG. 4, the green lens 23 permits the user to view the red umbrella image 32 therethrough. In this regard, the green lens 23 imparts a green component to the red color of the image 32 to render a resulting gray umbrella image 33 at the right eye of the user 40. The red and green components are complimentary colors, and when mixed together, form a gray image.

The red lens 25, as described previously in connection with FIG. 3, cancels or blocks the red umbrella image 32 and thus provides a red blank image 35 at the left eye of the user. As indicated diagrammatically in FIG. 4, the mind of the user processes an umbrella image 37 based upon the information received from the right eye which is able to see the gray umbrella image 33.

Similarly, the green umbrella image 36 is seen as a gray umbrella image through the red lens 25. In this manner, the user 40 is then able to match the umbrella image sheets 14 and 16. In so doing, the user must rely on information received at both eyes.

Figure 5:
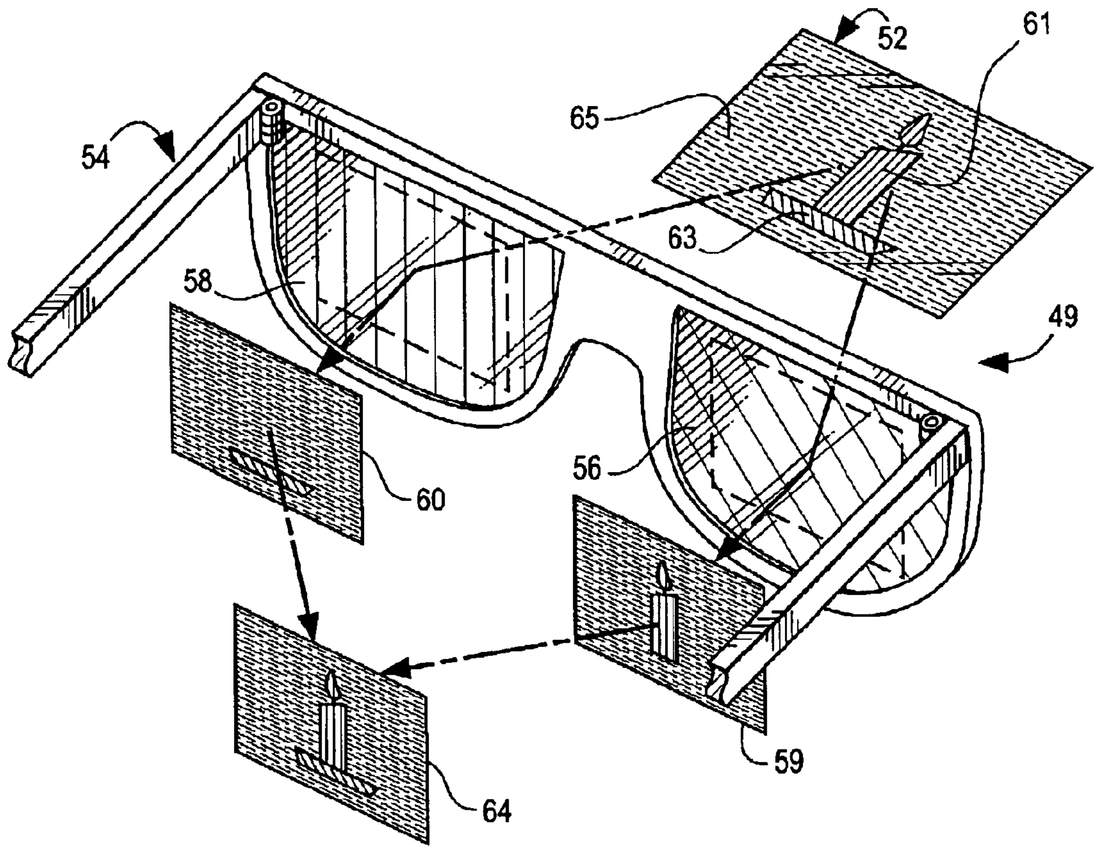
FIG. 5 is a pictorial, partially diagrammatic view of another vision therapy system, which is constructed in accordance with another example of the present invention, and which is illustrated from the point of view of the user.

Referring now to FIG. 5, there is shown a vision therapy system 49, which is constructed in accordance with another embodiment of the present invention. The system 49 includes one or more image bearing cards or sheets such as an image sheet 52. A pair of eyeglasses 54 having a green lens 56 and a red lens 58 is similar to the pair of eyeglasses 21 of FIG. 1.

Image sheet 52 has, on the face thereof, a grayish-red candle image 61 mounted in a grayish-green candle holder image 63. A gray background image 65 surrounds the images 61 and 63.

In use, when the user views the sheet 52 through the green lens with the right eye, he or she is able to see the red candle image 61, but not the green candle holder image 63, through the green lens 56 as indicated at 59 at the right eye of the user. In this regard, the green lens 56 adds a green component to the gray background to cancel or block the grayish-green candle holder image 63. Thus, the user is unable to distinguish the grayish-green candle holder image 63 from the gray background image 65 which is rendered grayish-green in color by the green lens 56.

Similarly, the red lens 58 adds a reddish component to the gray background 65 so that the grayish-red candle image 61 is unable to be distinguished from the gray background 65 as viewed through the red lens 58. Thus, as indicated at 60, an image is formed at the left eye of the user of the candle holder image only, and the candle image is not seen.

As indicated in FIG. 5, the images received at both the left and right eyes as indicated at 59 and 60, are then combined in the mind of the user as indicated at 64 to visualize the entire image of both the candle and its holder.

Figure 6:
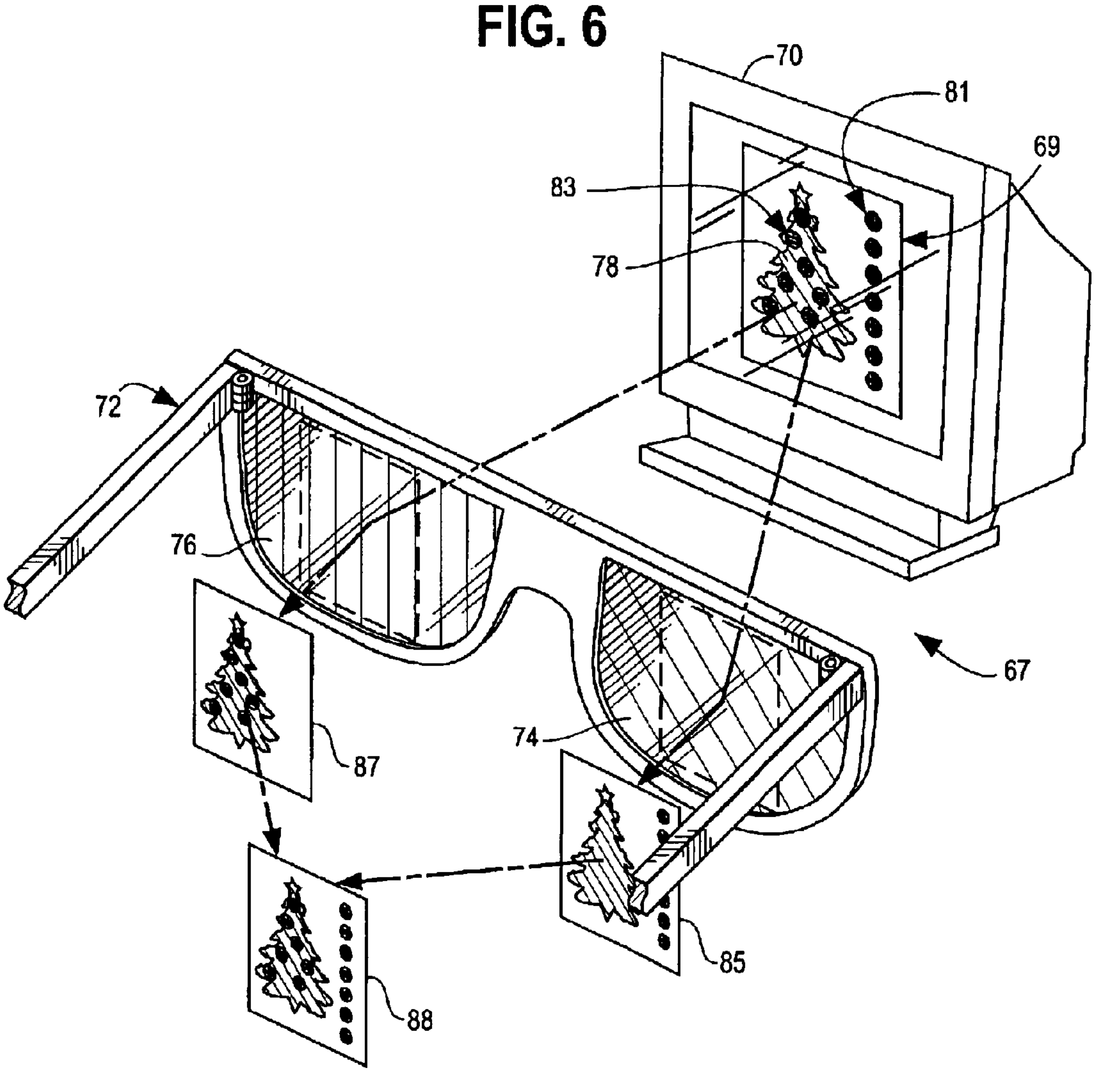
FIG. 6 is a pictorial, partially diagrammatic view of yet another vision therapy system, which is constructed in accordance with yet another embodiment of the present invention, and which is also illustrated from the point of view of the user.

Referring now to FIG. 6, a vision therapy system 67 is illustrated and is constructed in accordance with yet another embodiment of the present convention. The system 67 includes an image 69 produced by a computer display 70. A pair of eyeglasses having a green lens 74 and a red lens 76 is similar to the pair of eyeglasses 21 of FIG. 1. The pair of eyeglasses 72 are worn by the user and are adapted to enable the user to play a game to amuse oneself while undergoing vision therapy.

The image 69 includes a green Christmas tree image 83 and a set of red ornament images 81 to be matched with a corresponding set of gray ornament images 83 disposed on the green background Christmas tree image 78. In this regard, the images on the computer display 70 may be produced by suitable computer software, and enable the user to move the red ornament images 81 to the corresponding positions of the gray ornament images 83 on the Christmas tree image 78.

The green lens 74 of the pair of eyeglasses 72 permit the right eye of the user to visualize the green Christmas tree image 78 and the red ornament images 81, but not the gray ornament images 83. In this regard, the green lens 74 imparts a green color component to the gray ornament images 83 so that they may not be distinguished from the green background provided by the green Christmas tree image 78. Thus, as indicated at 85, the resulting image at the right eye of the user is without the gray ornament images 83.

Similarly, the red lens 76 causes the gray ornament images 83 to have a reddish gray color which contrasts with the green background provided by the green Christmas tree image 78. However, the background of the image 69 is rendered reddish in color by the red lens 76 so that the red ornament images 81 are indistinguishable therefrom. Thus, as indicated at 87, at the left eye of the user, only the Christmas tree image 78 and the gray ornament images 83 are seen through the red lens 76, and not the red ornament images 81.

As indicated diagrammatically at 88, the two different images seen at the eyes of the user are combined in the user's mind to reconstruct the complete image 69.

Although the present invention has been described in terms of certain embodiments of the invention, other embodiments apparent to those of ordinary skilled in the art also are within the scope of this invention. Thus, various changes and modifications may be made without departing from the spirit and scope of the invention. Moreover, not all of the features, aspects and advantages are necessarily required to practice the present invention. Accordingly, the scope of the present invention is intended to be defined only by the claims that follow.

What is claimed is:

1. A vision therapy method comprising:

displaying a red image;

displaying a green image; and displaying an image of a gray background for the green image to enable the viewing of the green image through a red lens to add a red component to the green image for causing the combined red and green image to appear gray to conceal it from view against the gray background.

2. The vision therapy method according to claim 1, further including displaying an image of a second gray background for the red image to enable the viewing of the red image through a green lens to add a green component to the red image for causing the combined green and red image to appear gray to conceal it from view against the second gray background.

3. The vision therapy method according to claim 2, wherein the red and green lenses form parts of a pair of eyeglasses.

4. The vision therapy method according to claim 1, wherein each one of said displaying steps includes providing a sheet or a portion thereof upon which is printed its image.

5. The vision therapy method according to claim 1, wherein each one of said displaying steps includes causing the displaying of its image to appear on a screen.

6. The vision therapy method comprising:

displaying a grayish green image; displaying a grayish red image; and displaying an image of a gray background for the grayish green image to enable the grayish green image to be viewed through a green lens to add a green component to the gray background to cause the background to conceal the grayish green image from view.

7. The vision therapy method according to claim 6, further including displaying a grayish red image to enable the grayish red image to be viewed through a red lens to add a red component to the gray background to cause the background to conceal the grayish red image from view.

8. The vision therapy method according to claim 7, further including displaying an image of a second gray background for the grayish red image to enable the viewing of the grayish red image through a green lens to add a green component to the grayish red image for causing the combined green and grayish red image to appear gray to conceal it from view against the second gray background.

9. The vision therapy method according to claim 7, wherein each one of said displaying steps includes providing a sheet upon which is printed its image.

10. The vision therapy method according to claim 7, wherein each one of said displaying steps includes causing the displaying of its image to appear on a screen.

11. A vision therapy method, comprising:

displaying a first color image;

displaying a second color image; and displaying a gray image associated with at least one of the above-mentioned images to selectively conceal from view against the gray image at least a portion of one of the color images when viewed through a colored lens.

12. The vision therapy method according to claim 11, wherein said first and said second colors are complimentary colors.

13. The vision therapy method according to claim 12, wherein said colors are red and green.

14. The vision therapy method according to claim 11, further providing a pair of eyeglasses bearing lens of the first and second colors.

15. The vision therapy method according to claim 11, wherein each one of said displaying steps includes providing a sheet upon which is printed its image.

16. The vision therapy method according to claim 11, wherein each one of said displaying steps includes causing the displaying of its image to appear on a screen.

17. A vision therapy system comprising:

first a device for displaying a red image;

second a device for displaying a green image; and third a device for displaying an image of a gray background for the green image to enable the viewing of the green image through a red lens to add a red component to the green image for causing the combined red and green image to appear gray to conceal it from view against the gray background.

18. The vision therapy system according to claim 17, further including a fourth device for displaying an image of a second gray background for the red image to enable the viewing of the red image through a green lens to add a green component to the red image for causing the combined green and red image to appear gray to conceal it from view against the second gray background.

19. The vision therapy system according to claim 18, wherein the red and green lenses form parts of a pair of eyeglasses.

20. The vision therapy system according to claim 17, wherein each one of said devices includes providing a sheet or a portion thereof upon which is printed its image.

21. The vision therapy system according to claim 17, wherein each one of said devices includes a computer screen for causing the displaying of its image to appear thereon.

22. A vision therapy system comprising:

a first device for displaying a grayish green image; a second device for displaying a grayish red image; and a third device for displaying an image of a gray background for the grayish green image to enable the grayish green image to be viewed through a green lens to add a green component to the gray background to cause the background to conceal the grayish green image from view.

23. The vision therapy system according to claim 22, further including a third device for displaying a grayish red image to enable the grayish red image to be viewed through a red lens to add a red component to the gray background to cause the background to conceal the grayish red image from view.

24. The vision therapy system according to claim 23, further including a fourth device for displaying an image of a second gray background for the grayish red image to enable the viewing of the grayish red image through a green lens to add a green component to the grayish red image for causing the combined green and grayish red image to appear gray to conceal it from view against the second gray background.

25. The vision therapy system according to claim 23, wherein each one of said devices includes a sheet upon which is printed its image.

26. The vision therapy system according to claim 23, wherein each one of said devices includes a computer screen for causing the displaying of its image to appear.

27. A vision therapy system, comprising:

a first device for displaying a first color image;

a second device for displaying a second color image; and a third device for displaying a gray image associated with at least one of the above-mentioned images to selectively conceal from view against the gray image at least a portion of one of the color images when viewed through a colored lens.

28. The vision therapy system according to claim 27, wherein said first and said second colors are complimentary colors.

29. The vision therapy system according to claim 28, wherein said colors are red and green.

30. The vision therapy system according to claim 27, further providing a pair of eyeglasses bearing lens of the first and second colors.

31. The vision therapy system according to claim 27, wherein each one of said devices includes providing a sheet upon which is printed its image.

32. The vision therapy system according to claim 27, wherein each one of said devices includes causing the displaying of its image to appear on a screen.

33. A vision therapy system comprising:

means for displaying a red image;

means for displaying a green image; and means for displaying an image of a gray background for the green image to enable the viewing of the green image through a red lens to add a red component to the green image for causing the combined red and green image to appear gray to conceal it from view against the gray background.

34. The vision therapy system according to claim 33, further including means for displaying an image of a second gray background for the red image to enable the viewing of the red image through a green lens to add a green component to the red image for causing the combined green and red image to appear gray to conceal it from view against the second gray background.

35. The vision therapy system according to claim 34, wherein the red and green lenses form parts of a pair of eyeglasses.

36. The vision therapy system according to claim 33, wherein each one of said means includes providing a sheet or a portion thereof upon which is printed its image.

37. The vision therapy system according to claim 33, wherein each one of said means includes computer screen means for causing the displaying of its image to appear thereon.

38. A vision therapy system comprising:

means for displaying a grayish green image; means for displaying a grayish red image; and means for displaying an image of a gray background for the grayish green image to enable the grayish green image to be viewed through a green lens to add a green component to the gray background to cause the background to conceal the grayish green image from view.

39. The vision therapy system according to claim 38, further including means for displaying a grayish red image to enable the grayish red image to be viewed through a red lens to add a red component to the gray background to cause the background to conceal the grayish red image from view.

40. The vision therapy system according to claim 38, further including means for displaying an image of a second gray background for the red image to enable the viewing of the red image through a green lens to add a green component to the red image for causing the combined green and red image to appear gray to conceal it from view against the second gray background.

41. The vision therapy system according to claim 38, wherein each one of said means includes a sheet upon which is printed its image.

42. The vision therapy system according to claim 38, wherein each one of said means includes a computer screen for causing the displaying of its image to appear.

43. A vision therapy system, comprising:

means for displaying a first color image;

means for displaying a second color image; and means for displaying a gray image associated with at least one of the above-mentioned images to selectively conceal from view against the gray image at least a portion of one of the color images when viewed through a colored lens.

44. The vision therapy system according to claim 43, wherein said first and said second colors are complimentary colors.

45. The vision therapy system according to claim 44, wherein said colors are red and green.

46. The vision therapy system according to claim 43, further providing a pair of eyeglasses bearing lens of the first and second colors.

47. The vision therapy system according to claim 43, wherein each one of said means includes providing a sheet upon which is printed its image.

48. The vision therapy system according to claim 43, wherein each one of said means includes causing the displaying of its image to appear on a screen.

* * * * *